(12) United States Patent
Nakamura et al.

(10) Patent No.: US 10,444,484 B2
(45) Date of Patent: Oct. 15, 2019

(54) SLIT LAMP MICROSCOPE

(71) Applicant: TAKAGI SEIKO CO., LTD., Nakano-shi, Nagano (JP)

(72) Inventors: Tomoyuki Nakamura, Nakano (JP); Shigeo Kanazawa, Nakano (JP); Takeshi Nara, Nakano (JP)

(73) Assignee: TAKAGI SEIKO CO., LTD., Nakano-Shi, Nagano (JP)

( * ) Notice: Subject to any disclaimer, the term of this patent is extended or adjusted under 35 U.S.C. 154(b) by 15 days.

(21) Appl. No.: 15/699,497

(22) Filed: Sep. 8, 2017

(65) Prior Publication Data

US 2018/0172969 A1 Jun. 21, 2018

(30) Foreign Application Priority Data

Dec. 21, 2016 (JP) ................ 2016-248138

(51) Int. Cl.
*G02B 21/02* (2006.01)
*G02B 21/04* (2006.01)
(Continued)

(52) U.S. Cl.
CPC ............ *G02B 21/025* (2013.01); *A61B 3/135* (2013.01); *G02B 21/04* (2013.01); *G02B 21/06* (2013.01); *G02B 21/22* (2013.01)

(58) Field of Classification Search
CPC ...... G02B 21/025; G02B 21/04; G02B 21/06; G02B 21/22; G02B 21/0012; G02B 21/0016; A61B 3/135
(Continued)

(56) References Cited

U.S. PATENT DOCUMENTS 2,765,702 A 10/1956 Sachtleben
4,518,231 A 5/1985 Muchel et al.
(Continued)

FOREIGN PATENT DOCUMENTS

EP 1905349 A1 * 4/2008 ............ A61B 3/135
EP 1905349 A1 4/2008
(Continued)

OTHER PUBLICATIONS

Extended European Search Report for European Application No. 17190392.5, dated Apr. 25, 2018.

*Primary Examiner* — Frank G Font
(74) *Attorney, Agent, or Firm* — Birch, Stewart, Kolasch & Birch, LLP (57) ABSTRACT

The slit lamp microscope comprises: a slit light optical system including a slit lamp, and a reflecting mirror or prism for reflecting a slit light from the slit lamp toward an eye of an examinee; and a microscope unit including an object lens, binocular eyepiece lenses, a magnification changing section, which changes magnifications of an image formed by light passing through the optical paths, being provided between the object lens and the eyepiece lenses, and an inward angle changing section, which changes a binocular viewing angle, being provided therebetween. A focal distance of the object lens is made shorter, by an optical path length of the inward angle changing section, than that of an object lens equipped with no inward angle changing section. The inward angle changing section is located closer to the object lens than to the magnification changing section.

2 Claims, 7 Drawing Sheets

(51) Int. Cl.
*G02B 21/06* (2006.01)
*G02B 21/22* (2006.01)
*A61B 3/135* (2006.01)

(58) Field of Classification Search
USPC .................................. 359/376, 381, 432
See application file for complete search history.

(56) References Cited

U.S. PATENT DOCUMENTS

| | | | |
|---|---|---|---|
| 4,838,671 | A | 6/1989 | Papritz et al. |
| 2008/0079901 | A1 | 4/2008 | Nakamura |
| 2008/0278800 | A1* | 11/2008 | Widmer .................. A61B 3/132 359/376 |
| 2011/0038040 | A1* | 2/2011 | Abele ...................... A61B 3/10 359/377 |
| 2014/0094784 | A1* | 4/2014 | Charles ................. A61F 9/0079 606/4 |
| 2017/0035608 | A1* | 2/2017 | Boxer Wachler ....... A61F 9/008 |

FOREIGN PATENT DOCUMENTS

| | | | |
|---|---|---|---|
| JP | 58-203411 | A | 11/1983 |
| JP | 62-269923 | A | 11/1987 |
| JP | 11-281894 | A | 10/1999 |
| JP | 2008-86435 | A | 4/2008 |

\* cited by examiner

SLIT LAMP MICROSCOPE

CROSS-REFERENCE TO RELATED APPLICATION

This application is based upon and claims the benefit of priority of the prior Japanese Patent Application No. P2016-248138, filed on Dec. 21, 2016, and the entire contents of which are incorporated herein by reference.

FIELD

The present invention relates to a slit lamp microscope for observing an eye of an examinee with a slit lamp.

BACKGROUND

A slit lamp microscope is used, by an ophthalmologist, for observing an eye (an anterior eye part) of an examinee.

A conventional slit lamp microscope will be explained.

The slit lamp microscope irradiates an eye of an examinee with a slit light from an oblique direction so as to visualize and observe transparent or semi-transparent tissues. The slit lamp microscope has a slit light optical system for emitting the slit light and a microscope unit for observing the eye of the examinee.

The microscope unit includes an object lens and a pair of binocular eyepiece lenses. A magnification changing section for changing observation magnification and an inward angle changing section for changing a binocular inward angle are provided between an object lens and the binocular eyepiece lenses (see PTL1: JP-A-S62-269923 and PTL 2: JP-A-2008-86435).

For example, a prism is used as the inward angle changing section.

SUMMARY OF INVENTION

Technical Problem

In case that the conventional microscope unit includes the inward angle changing section and that a distance between the object lens and the eye of the examinee is fixed, the eyepiece lenses of the microscope unit must be moved toward an observer.

When the eyepiece lenses are set close to the observer, a distance between the examinee and the observer (a reaching distance) must be long, so this structure causes a problem that it is difficult for the physically small observer to reach and handle an operation part.

Accordingly, it is an object to provide a slit lamp microscope in which a microscope unit includes an inward angle changing section and which is capable of preventing increase of a reaching distance.

Solution to Problem

To achieve the object, the present invention has following structures.

Namely, the slit lamp microscope of the present invention comprises:

a slit light optical system including a slit lamp for emitting a slit light, and a reflecting mirror or prism for reflecting the slit light emitted from the slit lamp toward an eye of an examinee;

a microscope unit including an object lens, binocular eyepiece lenses, a magnification changing section, which respectively changes magnifications of an image formed by light passing through the optical paths, being provided between the object lens and the binocular eyepiece lenses, and an inward angle changing section, which changes a binocular viewing angle, being provided therebetween; and a supporting section being extended downward from the magnification changing section for supporting the microscope unit.

Further, a focal distance of the object lens is made shorter, by an optical path length of the inward angle changing section, than that of an object lens equipped with no inward angle changing section, and the inward angle changing section is located closer to the object lens than to the magnification changing section equipped with the supporting section.

With the above described structure, in comparison with a case of providing no inward angle changing section to a microscope unit, the inward angle changing section can be located closer to the eye of the examinee without changing a position of the supporting section (i.e., without changing positions of the eyepiece lenses).

By locating the inward angle changing section closer to the eye of the examinee than to the magnification changing section equipped with the supporting section, the positions of the eyepiece lenses can be located at the same positions as those of the eyepiece lenses of the conventional microscope unit. Therefore, increase of a reaching distance can be prevented and enough operability can be secured even if the inward angle changing section is provided.

In the slit lamp microscope, the inward angle changing section and the object lens may constitute one inward angle changing unit which can be attached to and detached from the magnification changing section.

With this structure, even in a slit lamp microscope including no inward angle changing section, the inward angle can be changed by detaching the conventional object lens and attaching the inward angle changing unit.

In the slit lamp microscope, the inward angle changing section may be capable of moving between a position in the optical paths and a position outside the optical paths.

By locating the inward angle changing section in the optical paths, a stereo-vision region can be made wider but darker. Thus, the stereo-vision region can be made brighter by moving the inward angle changing section to the position outside the optical paths.

Advantageous Effect of Invention

By the present invention, the slit lamp microscope, in which the microscope unit includes the inward angle changing section and which is capable of preventing increase of the reaching distance of the observer and securing enough operability, can be provided.

BRIEF DESCRIPTION OF THE DRAWINGS

Embodiments of the present invention will now be described by way of examples and with reference to the accompanying drawings, in which.

DETAILED DESCRIPTION OF THE EMBODIMENTS

Preferred embodiments of the present invention will now be described in detail with reference to the accompanying drawings.

A whole structure of a slit lamp microscope 30 of the present embodiment will be explained with reference to FIGS. 1 and 2.

The slit lamp microscope 30 comprises: a slit lamp optical system 35 including a slit lamp 32 for emitting a slit light and a reflecting mirror 34 for reflecting the slit light emitted from the slit lamp 32 toward an eye of an examinee; and a microscope unit 38 for observing the eye of the examinee.

In the present embodiment, the slit lamp 32 emits the slit light downward, and the reflecting mirror 34 is provided under the slit lamp 32. Note that, an inner structure of the slit lamp 32 is publicly known, so explanation of the inner structure will be omitted.

A chin supporting section 36, on which a chin of the examinee will be mounted, is provided to the slit lamp microscope 30. The chin supporting section 36 is provided between two supporting pillars 37, which are extended in the vertical direction. A forehead contact section 33, with which the examiner will bring his forehead into contact, is provided above the chin supporting section 36. The forehead contact section 33 is also provided between the two supporting pillars 37.

When observing the eye of the examinee whose chin is mounted on the chin supporting section 36, the microscope unit 36 is located to face the chin supporting section 36 and the forehead contact section 33 across the reflecting mirror 34.

The microscope unit 38 is attached to a supporting section 41 which is extended upward from a supporting base 40.

The slit lamp 32 and the reflecting mirror 34, which are connected by connection arms 39, are also attached to the supporting base 40.

The supporting base 40 is mounted on a frame 42 and capable of precisely moving thereon. Therefore, the microscope unit 38, the slit lamp 32 and the reflecting mirror 34 can be precisely moved, with respect to the frame 42, with the movement of the supporting base 40

On the other hand, the supporting pillars 37, to which the chin supporting section 36 is attached, are fixed to the frame 42. Therefore, an irradiation position of the eye to be examined, to which the slit light will be emitted, can be precisely adjusted by precisely moving the supporting base 40 with respect to the eye.

The supporting base 40 can be precisely moved by operating a joystick 44.

Figure 3:
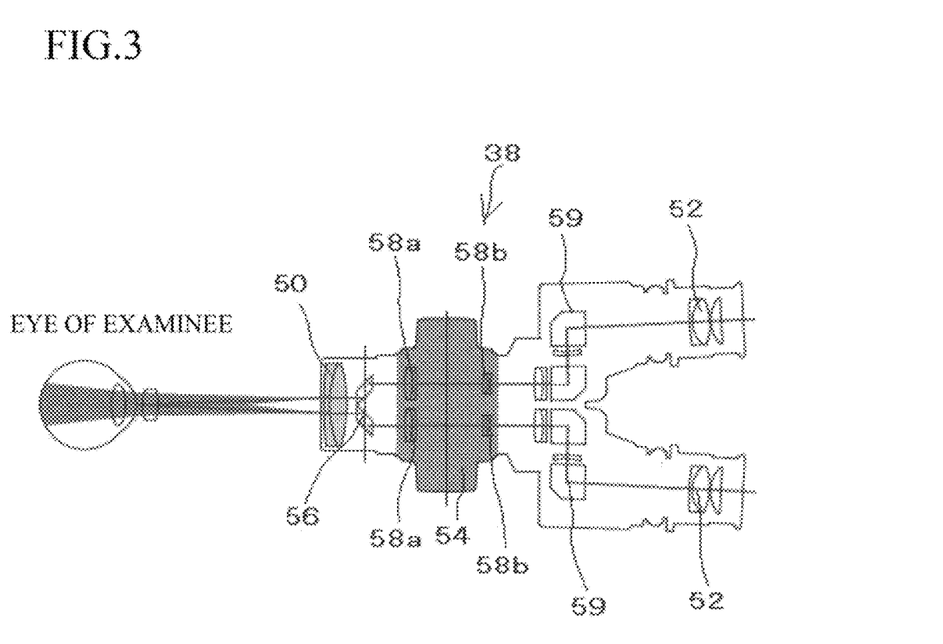
FIG. 3 is a plan view of a microscope unit showing a schematic structure.

The structure of the microscope unit 38 of the present embodiment will be explained with reference to FIG. 3.

The microscope unit 38 includes: an object lens 50; a pair of binocular eyepiece lenses 52; a magnification changing section 54, which respectively changes magnifications of an image formed by light passing through the optical paths, being provided between the object lens 50 and the binocular eyepiece lenses 52; and an inward angle changing section 56, which changes a binocular viewing angle, being provided therebetween.

Figure 1:
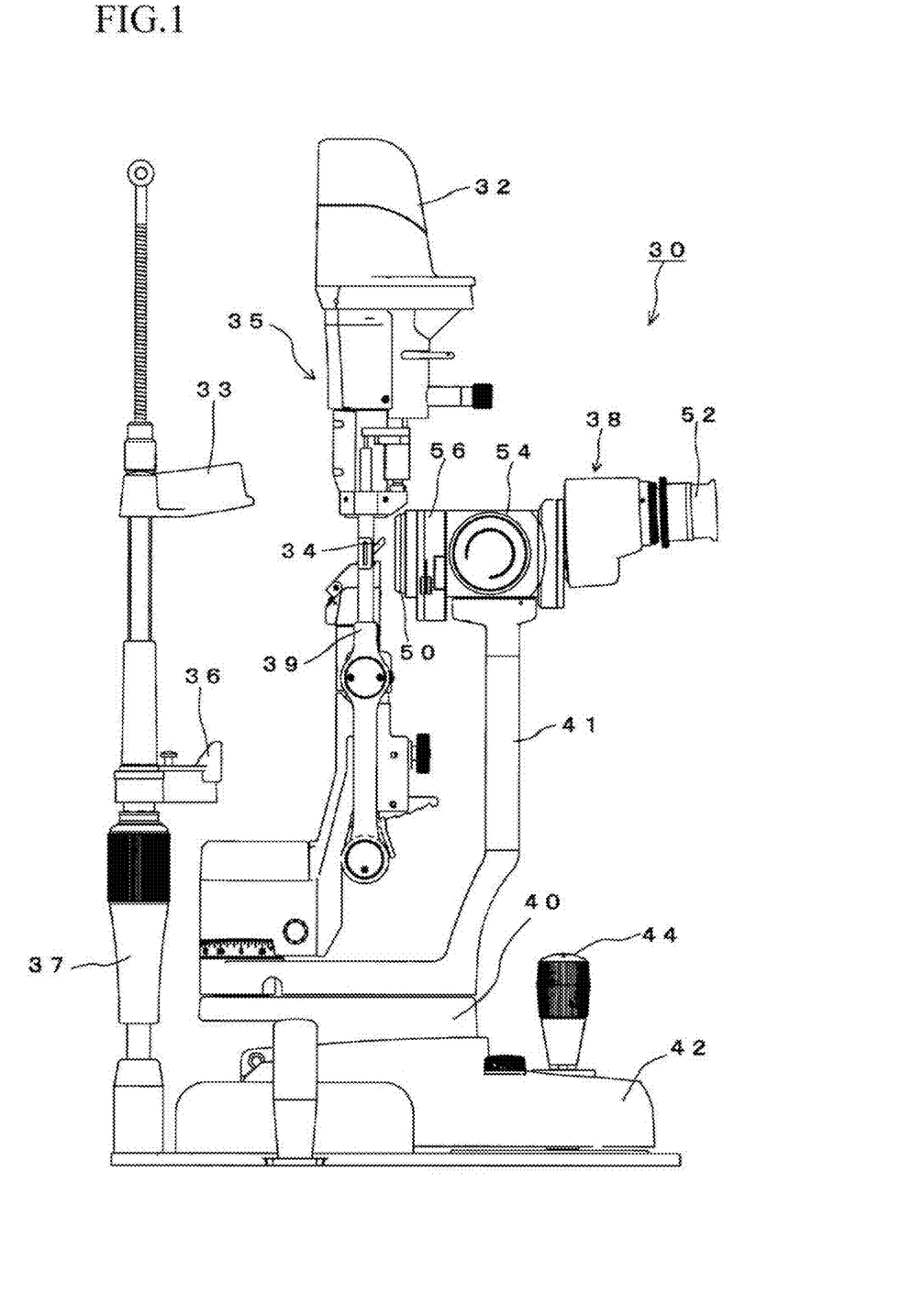
FIG. 1 is a side view of a slit lamp microscope of the present invention showing the entire structure.
Figure 2:
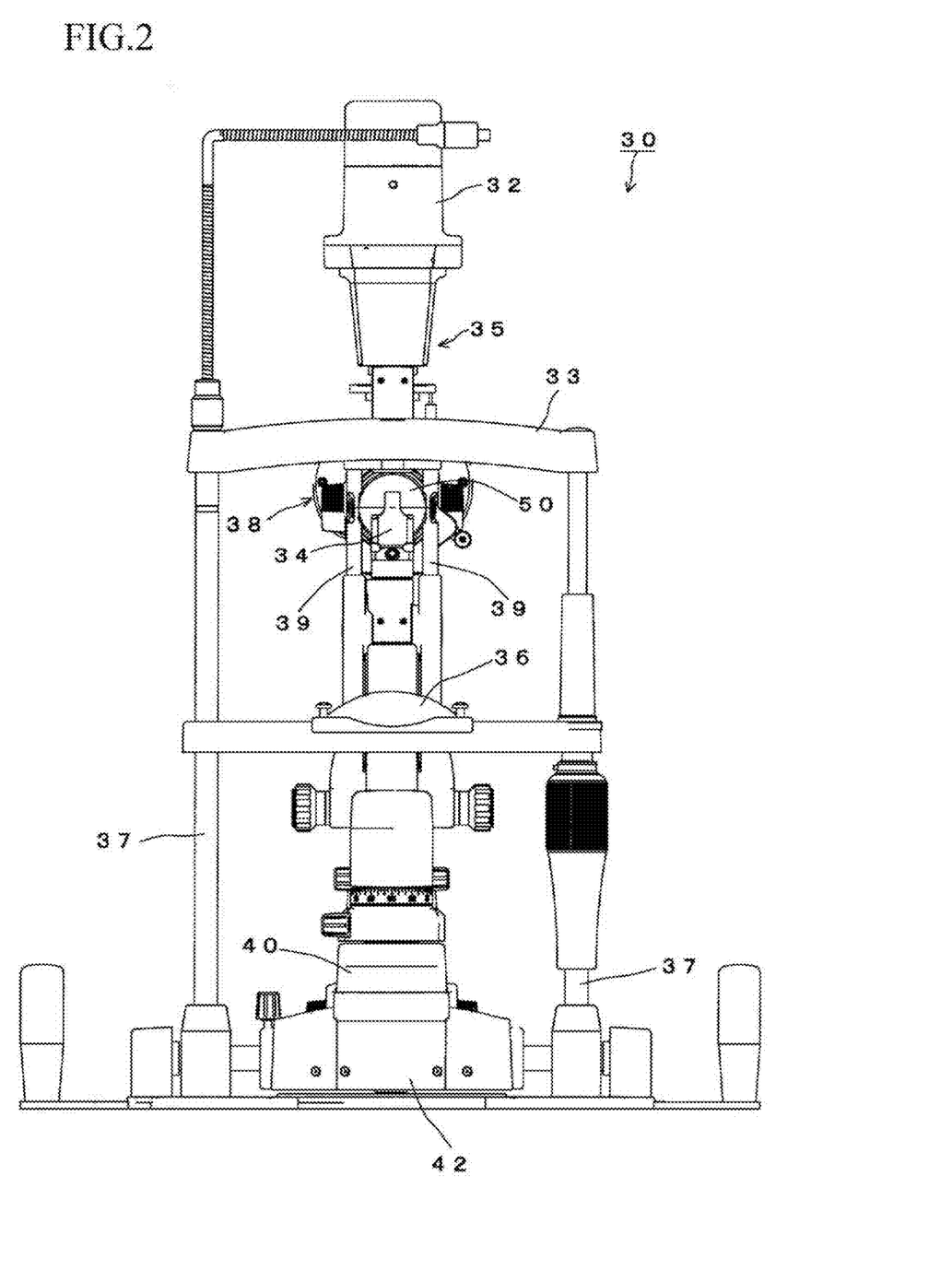
FIG. 2 is a front view of the slit lamp microscope showing the entire structure seen from an examinee.

As shown in FIG. 1, an upper end of the supporting section 41 is connected and fixed to the magnification changing section 54, so that the microscope unit 38 can be supported.

In the magnification changing section 54, a plurality of magnification changing lenses 58a and 58b are provided for each of optical paths so as to optionally adjust the magnifications.

Two prism sections 59 are provided. Each of the prism sections 59 is provided between each of the eyepiece lenses 52 and each of the magnification changing lenses 58b so as to adjust a distance between the two optical paths.

A prism for adjusting a width of each of the optical paths is employed as the inward angle changing section 56.

By providing the inward angle changing section 56, a stereo-vision region can be made wider.

Figure 4:
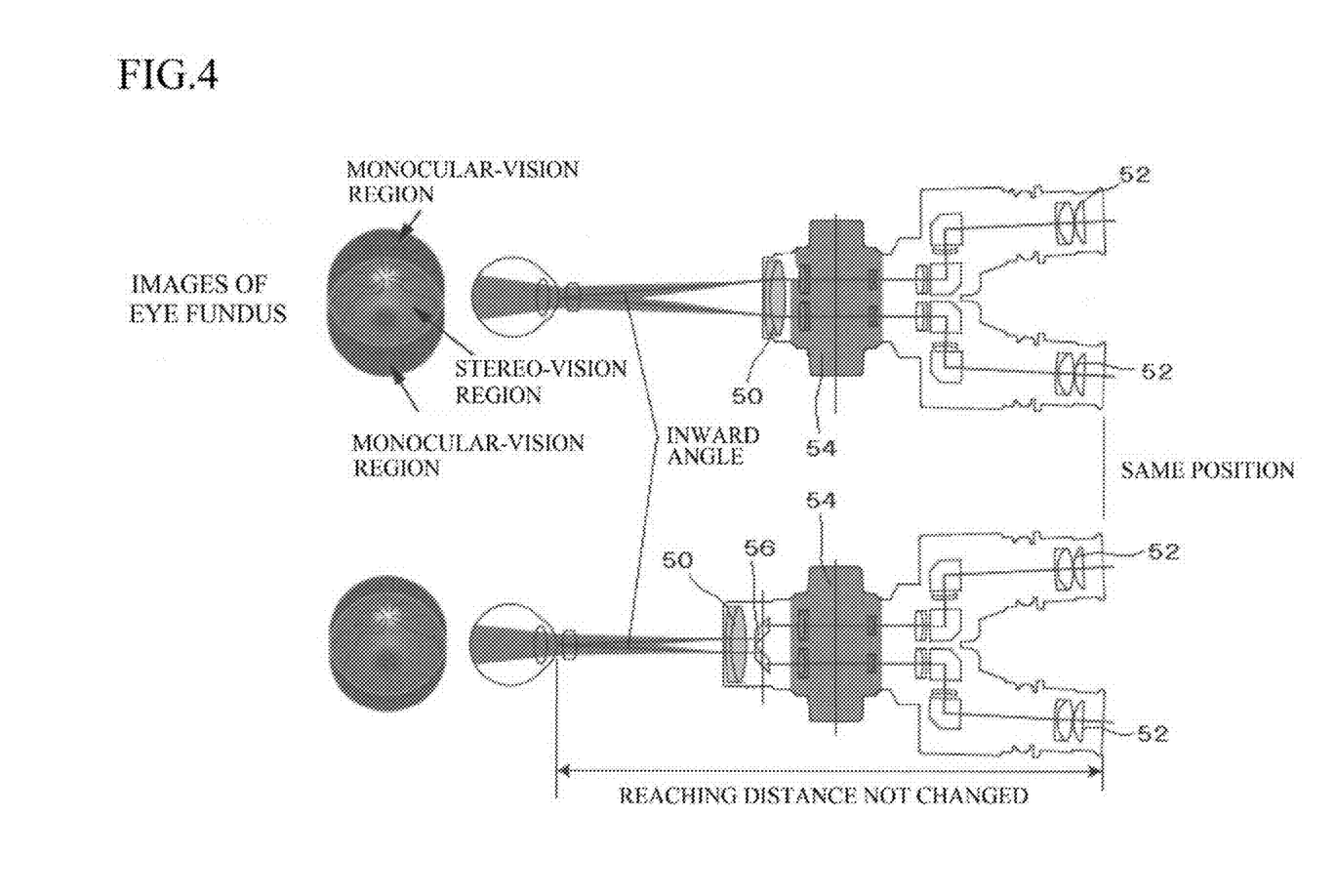
FIG. 4 is an explanation view of the microscope unit including an inward angle changing section and another microscope unit including no inward angle changing section.
Figure 5:
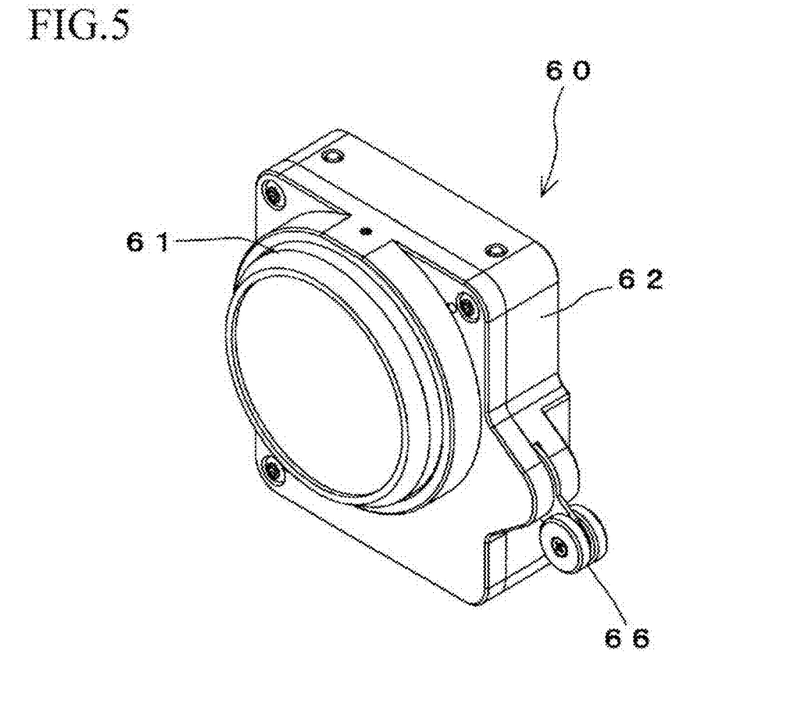
FIG. 5 is a perspective view of the inward angle changing section.
Figure 6:
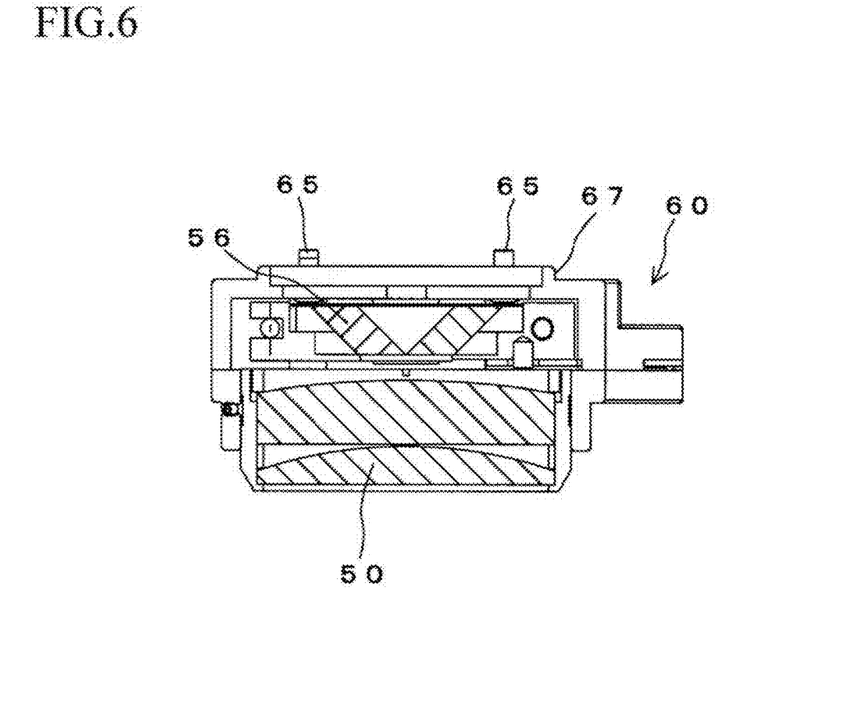
FIG. 6 is a plan view of the inward angle changing section showing an inner structure thereof.

As shown in FIG. 4, the inward angle changing section 56 is located closer to the object lens 50 (i.e., the examinee) than to the supporting section 41 attached to the magnification changing section 54. Even if the inward angle changing section 56 is provided, the positions of the eyepiece lenses 52 are located at the same positions as those of the eyepiece lenses of the conventional microscope unit having no inward angle changing section.

Concretely, a focal distance of the object lens 50 may be made shorter by an optical path length of the inward angle changing section 56.

Since the focal distance of the object lens 50 is made shorter than that of an object lens equipped with no inward angle changing section, the object lens 50 can be located close to the examinee. So, even if the inward angle changing section 56 is provided, a distance between the eye of the examinee and the eyepiece lenses 52 of the present embodiment can be made as same as that in the case of including no inward angle changing section.

In the present embodiment, an inward angle changing unit 60, in which the object lens 50 and the inward angle changing section 56 are integrated, is employed. The inward angle changing unit 60 can be attached to and detached from an examinee-side part of the magnification changing section 54.

The inward angle changing unit 60 are shown in FIGS. 5-9.

In the inward angle changing unit 60, the object lens 50 and a prism constituting the inward angle changing section 56 are accommodated in one case.

In the inward angle changing unit 60, a part accommodating the object lens 50 is formed into a cylindrical shape and projected toward the examinee; and a part accommodating the prism of the inward angle changing section 56 is formed into a thin rectangular parallelepiped shape.

Figure 7:
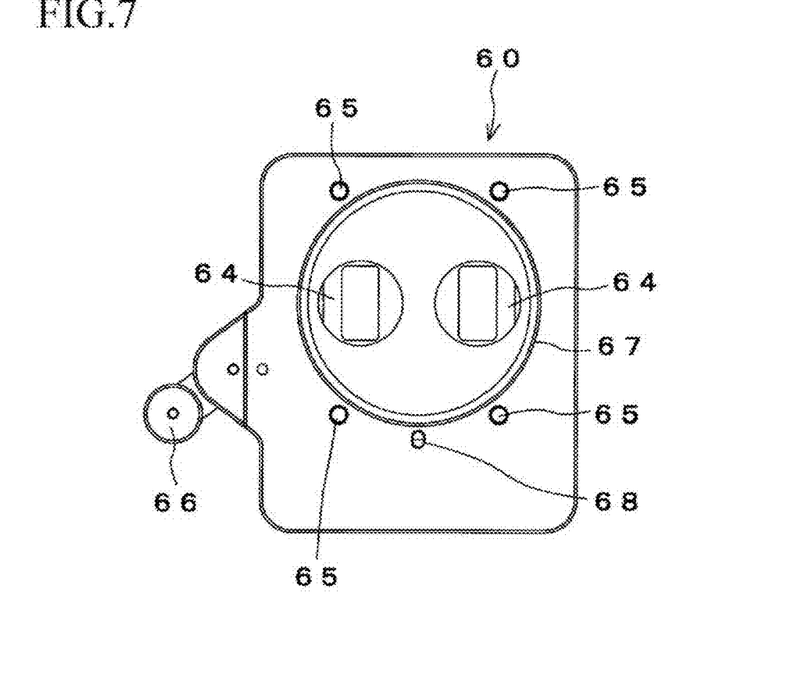
FIG. 7 is a rear view of the inward angle changing section.

Two circular openings 64 for forming the two optical paths are formed in a surface of the inward angle changing unit 60 on the magnification changing section 54 side.

A circular projection part 67, whose front shape is formed into a circular shape and which projects toward the magnification changing section 54, is formed in the surface of the inward angle changing unit 60 on the magnification changing section 54 side. Further, a long positioning hole 68, into which a positioning pin (not shown) of the magnification changing section 54 can be inserted, is formed in the same surface of the inward angle changing unit 60.

When the inward angle changing unit 60 is attached to the magnification changing section 54, the inward angle changing unit 60 is positioned by an outer circumference of the circular projection part 67 and the long positioning hole 68, and then fixed by screws 65.

Figure 8:
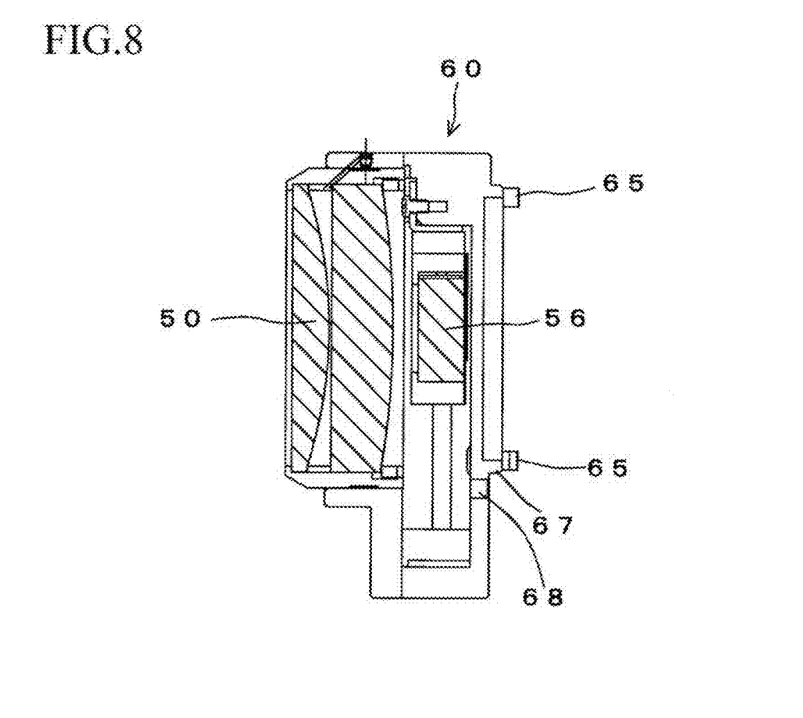
FIG. 8 is a side view of an inward angle changing unit showing an inner structure thereof in which the inward angle changing section is located in an optical path.
Figure 9:
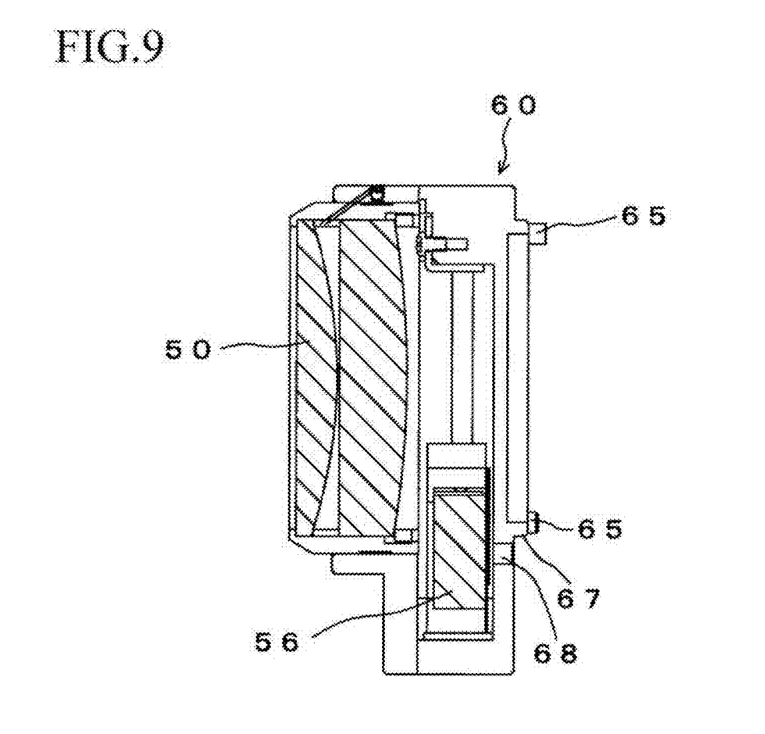
FIG. 9 is a side view of the inward angle changing unit showing the inner structure thereof in which the inward angle changing section is located outside of the optical path.

In the inward angle changing unit 60, the prism of the inward angle changing section 56 is capable of moving between a position in the optical paths and a position outside the optical paths.

A switching lever 66 is provided in a side surface of the inward angle changing unit 60. The switching lever 66 is linked with the prism of the inward angle changing section 56. The observer is capable of selectively moving the prism of the inward angle changing section 56 between the position in the optical paths and the position outside the optical paths by operating the switching lever 66.

In the present embodiment, when the switching lever 66 is moved upward obliquely from the outside of the unit toward the inside thereof, the prism of the inward angle changing section 56 is located in the optical paths; when the switching lever 66 is moved downward obliquely from the outside toward the inside, the prism of the inward angle changing section 56 is moved a position under the optical paths.

When the prism of the inward angle changing section 56 is located in the optical paths, a stereo-vision region is made wider and darker. On the other hand, when the prism of the inward angle changing section 56 is located outside the optical paths, the stereo-vision region is made narrower and brighter. Therefore, the observer can change the width and the brightness of the stereo-vision region according to conditions of observation objects.

In the above described embodiment, the inward angle changing section is moved upward and downward with respect to the optical paths so as to move the same between the position in the optical paths and the position outside the optical paths, but the present invention is not limited to the above described embodiment. For example, the inward angle changing section may be moved horizontally.

In the above described embodiment, the slit light is reflected by the reflecting mirror, but the present invention is not limited to the above described embodiment. For example, the slit light may be reflected by a prism. Further, the slit light may irradiate the reflecting mirror or prism from not only above but also below.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alternations could be made hereto without departing from the spirit and scope of the invention.

What is claimed is:

1. A slit lamp microscope, comprising:
    a slit light optical system including a slit lamp for emitting a slit light, and a reflecting mirror or prism for reflecting the slit light emitted from the slit lamp toward an eye of an examinee;
    a microscope unit including an object lens, binocular eyepiece lenses, a magnification changing section, which respectively changes magnifications of an image formed by light passing through optical paths, being provided between the object lens and the binocular eyepiece lenses, and an inward angle changing section, which changes a binocular viewing angle, being provided therebetween; and
    a supporting section being extended downward from the magnification changing section for supporting the microscope unit,
    wherein a focal distance of the object lens is made shorter, by an optical path length of the inward angle changing section, than that of an object lens equipped with no inward angle changing section,
    the inward angle changing section is located closer to the object lens than to the magnification changing section equipped with the supporting section, and
    wherein the inward angle changing section and the object lens constitute one inward angle changing unit which can be attached to and detached from the magnification changing section.

2. The slit lamp microscope according to claim 1, wherein the inward angle changing section is capable of moving between a position in the optical paths and a position outside the optical paths.

* * * * *